US008703180B1

(12) United States Patent
Stankus et al.

(10) Patent No.: US 8,703,180 B1
(45) Date of Patent: Apr. 22, 2014

(54) MULTIPLE GROWTH FACTOR COMPOSITIONS, METHODS OF FABRICATION, AND METHODS OF TREATMENT

(75) Inventors: John J. Stankus, Campbell, CA (US); Florian N. Ludwig, Mountain View, CA (US); Evgenia Mandrusov, Santa Clara, CA (US); Liangxuan Zhang, Palo Alto, CA (US); Hong Ma, Cupertino, CA (US); Jinping Wan, Sunnyvale, CA (US); Shubhayu Basu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 742 days.

(21) Appl. No.: 11/877,635

(22) Filed: Oct. 23, 2007

(51) Int. Cl.
*A61K 9/127* (2006.01)
*A61F 2/00* (2006.01)
*A61K 9/14* (2006.01)
*C12N 5/071* (2010.01)

(52) U.S. Cl.
USPC ............ 424/450; 424/423; 424/487; 435/366

(58) Field of Classification Search
None
See application file for complete search history.

(56) References Cited

U.S. PATENT DOCUMENTS

| | | | | |
|---|---|---|---|---|
| 5,043,165 | A | * | 8/1991 | Radhakrishnan ............. 424/450 |
| 2003/0157160 | A1 | * | 8/2003 | Budzynski et al. ............ 424/450 |
| 2004/0265367 | A1 | * | 12/2004 | Thorpe et al. .................. 424/450 |
| 2007/0003528 | A1 | * | 1/2007 | Consigny et al. ............ 424/93.7 |
| 2007/0218118 | A1 | * | 9/2007 | Michal et al. ................. 424/450 |
| 2007/0255422 | A1 | * | 11/2007 | Wei et al. .................... 623/23.51 |
| 2008/0015709 | A1 | * | 1/2008 | Evans et al. ................ 623/23.51 |

FOREIGN PATENT DOCUMENTS

WO WO 2005/053749 A2 6/2005

OTHER PUBLICATIONS

Musaro, A., et al., "The Role of local Insulin-like Growth Factor-1 Isoforms in the Pathophysiology of Skeletal Muscle," Current Genomics, 2002, pp. 149-162, 3(3).

Gallagher, Gabrielle L., et al., "Myocardial extracellular matrix remodeling in ischemic heart failure," Frontiers in Bioscience, Jan. 1, 2007, pp. 1410-1419, 12.
Felkin, Leanne E., et al., "A Quantitative Gene Expression Profile of Matrix Metalloproteinases (MMPS) and Their Inhibitors (TIMPS) in the Myocardium of Patients With Deteriorating Heart Failure Requiring Left Ventricular Assist Device Support," The Journal of Heart and Lung Transplantation, Dec. 2006, pp. 1413-1419, 25(12).
Graham, H.K., et al., "Spatial disruption and enhanced degradation of collagen with the transition from compensated ventricular hypertrophy to symptomatic congestive heart failure," Am. J. Physiol. Heart Circ. Physiol., Mar. 2007, pp. H1364-H1372, 292.
Spinale, Francis G., et al., "Time-Dependent Changes in Matrix Metalloproteinase Activity and Expression During the Progression of Congestive Heart Failure: Relation to Ventricular and Myocyte Function," Circulation Research, 1998, pp. 482-495, 82.
Cleland, John G.F., et al., "Clinical trials update from the American college of Cardiology meeting: Care-HF and the Remission of Heart Failure, Women's Health Study, TNT, Compass-HF, Veritas. Canpap, Peech and Premier," The European Journal of Heart Failure, 205, pp. 931-936, 7.
Mourkioti, Foteini, et al., "IGF-1, inflammation and stem cells: interactions during muscle regeneration," Trends in Immunology, Oct. 2005, pp. 535-542, 26(10).
Christman, Karen L., "Biomaterials for the Treatment of Myocardial Infarction," Journal of American College of Cardiology, Sep. 5, 2006, pp. 907-913, 48(5).
Urbanek, Konrad, "Cardiac Stem Cells Possess Growth Factor-Receptor Systems That After Activation Regenerate the Infarcted Myocardium, Improving Ventricular Function and Long-Term Survival," Circulation Research, Sep. 30, 2005, pp. 663-673, 97.

* cited by examiner

*Primary Examiner* — Doug Shultz
(74) *Attorney, Agent, or Firm* — Randy Shen; Blakely Sokoloff Taylor & Zafman LLP

(57) ABSTRACT

Disclosed are compositions with sustained-release carriers associated with at least two different types of growth factors and methods of fabrication and treatments thereof. In some embodiments, simultaneous release of the growth factors may be preferred while in other embodiments, sequential release of the growth factors may be preferred. Application of at least two growth factors to an injury site, e.g., compromised cardiac tissue caused by, for example, myocardial infarction or ischemic heart failure, may better mimic and induce the complex growth factor signaling pathways necessary to improve cardiac function. When applied to a patient after a myocardial infarction or ischemic heart failure, multiple growth factors within a sustained-release carrier platform or platforms may cause a synergistic effect on injected cells intending to alleviate left ventricle remodeling. Methods of treatment include percutaneous, sub-xiphoid, and open chest methods using catheters and/or syringes.

14 Claims, 3 Drawing Sheets

MULTIPLE GROWTH FACTOR COMPOSITIONS, METHODS OF FABRICATION, AND METHODS OF TREATMENT

FIELD OF THE INVENTION

Post-myocardial infarction compositions and methods of treatment.

BACKGROUND OF THE INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

An important component in the progression to heart failure is remodeling of the heart due to mismatched mechanical forces between the infarcted region and the healthy tissue resulting in uneven stress and strain distribution in the left ventricle (LV). Once an MI occurs, remodeling of the heart begins. The principle components of the remodeling event include myocyte death, edema and inflammation, followed by fibroblast infiltration and collagen deposition, and finally scar formation. The principle component of the scar is collagen. Since mature myocytes of an adult are not regenerated, the infarct region experiences significant thinning. Myocyte loss is the major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

Currently, methods to alleviate LV remodeling, including application of cells, biomaterials (also known as "bioscaffoldings"), or cell-loaded bioscaffoldings to an injury site (e.g., compromised heart tissue), have been preliminarily explored. Implantation of autologous cells for damaged myocardium is under current clinical investigation. In other recent studies, implanting biomaterials to an infarct region has been shown to improve the ejection fraction in rats. See Christman, K. L., *Biomaterials for the Treatment of Myocardial Infarction*, J. American College of Cardiology, vol. 48, no. 5 (2006). Limitations of current methods include low cell retention at the injury site and reduced long-term viability of injected or endogenous cells.

Growth factors are naturally occurring proteins secreted by many different cell types for signaling to induce cell migration, differentiation, survival, or proliferation, in addition to other functions. Signaling occurs through binding of factors to cell surface specific receptors. Signals can be amplified within the cell to regulate specific gene expression. Growth factors typically act in a dose- and time-dependent fashion with small variations in concentrations resulting in a biological effect. When applied in post-MI therapies, growth factors have the potential to increase the survival of cells whether endogenous or exogenous. Current growth factor therapies for both acute MI and HF have focused on bolus or systemic injection of a single growth factor type. Such therapies, however, are subject to a large percentage of the growth factor being washed away by blood flow thus minimizing the potential benefit of the treatment agent that may otherwise be obtained. Moreover, application of a single growth factor may not be as beneficial as previously hypothesized in view of naturally occurring complex growth factor signaling pathways.

SUMMARY OF THE INVENTION

A composition including a first bioerodable carrier platform capable of sustained release of a treatment agent, the composition including at least two different treatment agents, at least one of the two different treatment agents associated with the first bioerodable carrier platform wherein each treatment agent has a function, when delivered to compromised heart tissue, selected from the group consisting of cell survival, cell recruitment, angiogenesis, arteriogenesis, and anti-fibrotic development, and wherein the at least two different treatment agents have a different function relative to one another. The composition may further include at least one second different bioerodable carrier platform capable of sustained release of a treatment agent wherein a rate of release of the first bioerodable carrier platform is different relative to a rate of release of the second bioerodable carrier platform, and wherein one of the treatment agents is associated with the first bioerodable carrier platform and the other of the treatment agents is associated with the second different bioerodable carrier platform.

A method of treating compromised heart tissue within a mammal, including the process of advancing a delivery device through a lumen of a blood vessel to a treatment region wherein the treatment region is compromised heart tissue; and introducing a composition through the delivery device wherein the composition includes (i) a first bioerodable carrier platform capable of sustained release of a treatment agent; and (ii) at least two different treatment agents, at least one of the two different treatment agents associated with the first bioerodable carrier platform wherein the treatment agents have a function, when delivered to compromised heart tissue, selected from the group consisting of cell survival, cell recruitment, angiogenesis, arteriogenesis, and anti-fibrotic development, and wherein the at least two different treatment agents have a different function relative to one another.

DETAILED DESCRIPTION OF THE INVENTION

Figure 1A:
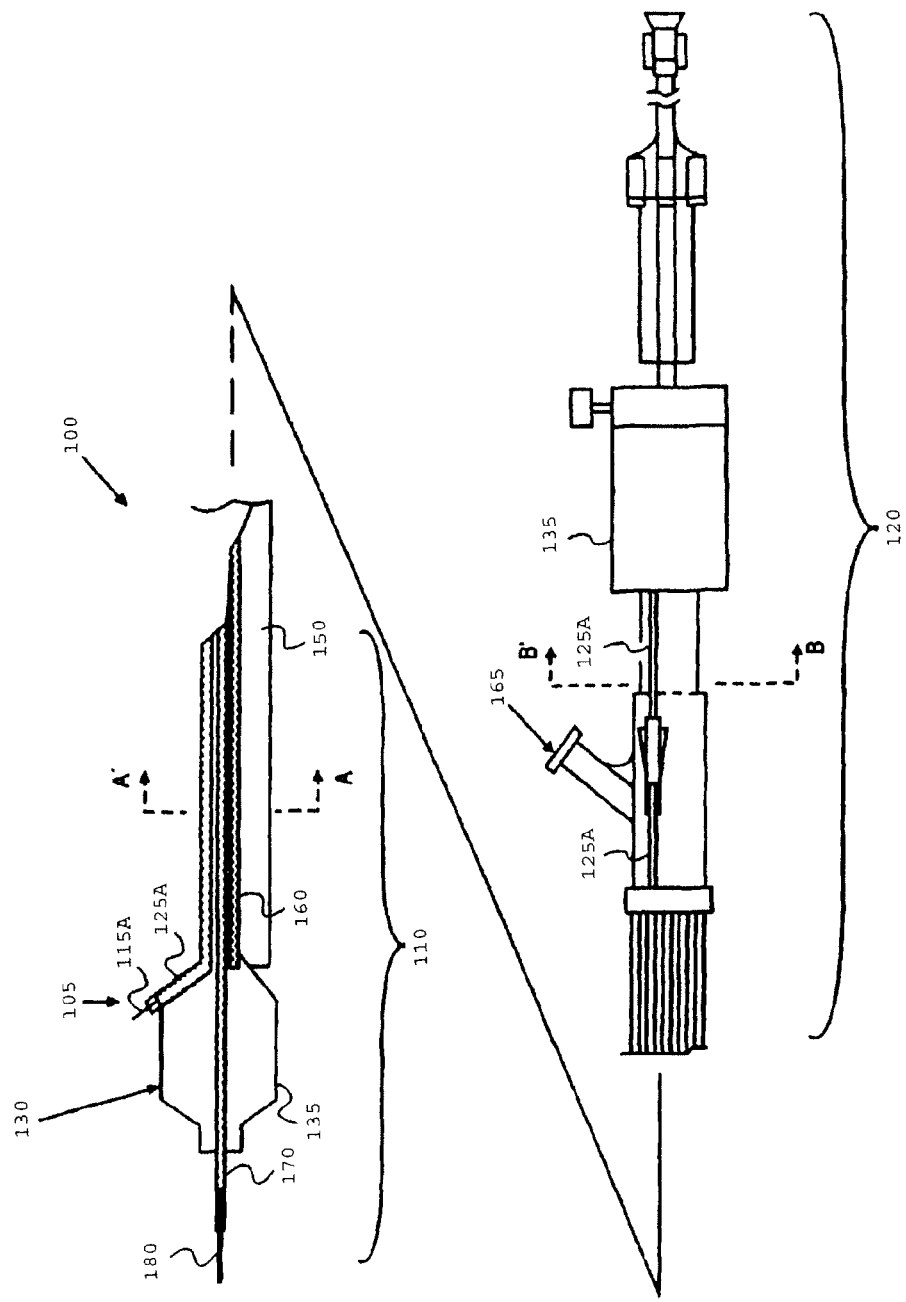
FIGS. 1A-1C illustrate an alternative embodiment of a dual-needle injection device which may be used to deliver core-shell particles in accordance with embodiments of the invention.

Embodiments of the invention include compositions comprised of sustained-release carriers associated with at least two different types of growth factors. In some embodiments, simultaneous release of the growth factors may be preferred while in other embodiments, sequential release of the growth factors may be preferred. It is anticipated that the application of at least two growth factors to an injury site, e.g., compromised cardiac tissue caused by, for example, myocardial infarction or ischemic heart failure, may better mimic and induce the complex growth factor signaling pathways necessary to improve cardiac function. In vitro results have demonstrated that multiple growth factors cause a synergistic effect on cultured cells, i.e., the effect of two factors is greater than the sum of their two-fold effect.

Carriers

According to embodiments of the invention, a bioerodable carrier platform associated with at least two treatment agents can be used for the sustained or controlled release of the treatment agents to achieve a synergistic effect to treat or prevent the formation of compromised cardiac tissue. In the context of this application, "associated with" means encapsulated, suspended, disposed within or on (chemisorbed) the carrier platform. The treatment agent(s) can be, for example, at least two different growth factors. It is anticipated that a sustained-release bioerodable carrier platform (or multiple sustained-release carrier platforms) associated with at least two growth factors may be beneficial by mimicking and inducing the complex growth factor signaling pathways necessary to improve cardiac function when applied to a post-MI infarct or HF region. Sustained-release carriers may include, but are not limited to: particles, such as microparticles, nanoparticles, or core-shell particles; fibers, such as, microfibers or nanofibers; vesicles, such as liposomes, polymerosomes, micelles, or microbubbles; or hydrogels (also known as "bioscaffoldings" when administered to compromised cardiac tissue) which may be formulated as a single component or a multiple component systems.

In one embodiment, the biodegradable carrier platform is a liposome. "Liposomes" are artificial vesicles that are approximately spherical in shape and can be produced from natural phospholipids, sphingolipids, ceramides, cholesterol or estradiol. Generally, a liposome has a lipid bilayer membrane encapsulating an aqueous solution, i.e., "core." The lipid bilayer membrane allows for fusion with an endogenous (or exogenous) cell membrane, which, similar to the liposome, comprises a semipermeable lipid bilayer. In one method, phospholipids and a treatment agent are mixed with estradiol in chloroform. Suitable phospholipids include, but are not limited to, dimyristoylphosphatidylcholine (DMPC), dipalmitoyl phosphatidyl ethanolamine (DPPE),1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-dioleoyl-sn-glycero-3-phosphocholine (DOPC), 1-dalmitoyl-2-oleoyl-sn-glycero-3-phosphocholine (POPC), egg phosphatidylcholine (EPC), hydrogenated egg phosphatidylcholine (HEPC), soybean phosphatidylcholine (SPC), hydrogenated soybean phosphatidylcholine (HSPC). The liposomes may also be hydrophilically modified by coating the liposomes with an agent such as poly(ethylene glycol) or dextran. Such coating tends to avoid detection from the body's immune system. After mixing, the solvent (and an optional co-solvent) can be evaporated with heat or ambient temperature in a round bottom flask. Resultant lipids will be deposited on the glass surface. The deposited lipid film can be re-suspended in aqueous solution to form multilamellar (or unilamellar) vesicles, and extruded to prepare appropriate sized liposomes. Liposomes can be in a range from about 25 nm to about 2000 nm. One of ordinary skill in the art will appreciate that the treatment agents to reside within the core of the liposome are likely substantially hydrophilic, as the core of the liposome is generally an aqueous environment.

In another embodiment, the biodegradable carrier platform is a polymerosome. "Polymerosomes" are polymer vesicles formed from di-block or tri-block copolymers with blocks of differing solubility. Diblock copolymers are known to spontaneously organize into polymer vesicles. Polymerosomes may be formed by methods such as film rehydration, electroformation and double emulsion. In some methods, a similar manufacturing technique can be used as that of a liposome to form polymerosomes. In some embodiments, a polymerosome can be a di-block copolymer including a block which is hydrophobic, e.g., poly(lactic acid), polycaprolactone, n-butyl acrylate, and another block which is hydrophilic, e.g., poly(ethylene glycol), poly(acrylic acid). A polymerosome can be in a range from between about 25 nm to about 2000 nm. One of ordinary skill in the art will appreciate that the hydrophobic and hydrophilic regions of the treatment agents will generally associate with the hydrophobic and hydrophilic regions of the polymerosome, respectively.

In another embodiment, the biodegradable carrier platform is a micelle. A "micelle" is an aggregate of surfactant or polymer molecules dispersed in a liquid colloid. Micelles are often globular in shape, but other shapes are possible, including ellipsoids, cylinders, bilayers, and vesicles. The shape of a micelle is controlled largely by the molecular geometry of its surfactant or polymer molecules, but micelle shape also depends on conditions such as temperature or pH, and the type and concentration of any added salt.

Micelles can be formed from individual block copolymer molecules, each of which contains a hydrophobic block and a hydrophilic block. The amphiphilic nature of the block copolymers enables them to self-assemble to form nanosized aggregates of various morphologies in aqueous solution such that the hydrophobic blocks form the core of the micelle, which is surrounded by the hydrophilic blocks, which form the outer shell. The inner core of the micelle creates a hydrophobic microenvironment for mimetic peptide, while the hydrophilic shell provides a stabilizing interface between the micelle core and an aqueous medium. Examples of polymers which can be used to form micelles include, but are not limited to, polycaprolactone polyethylene oxide blocks, polyethylene oxide-β-polypropylene oxide-β-polyethylene oxide triblock copolymer and copolymers which have a polypeptide or polylactic acid core-forming block and a polyethylene oxide block. A micelle can be in a range from between about 10 nm to about 100 nm. One of ordinary skill in the art will appreciate that the hydrophobic and hydrophilic regions of the treatment agent will generally associate with the hydrophobic and hydrophilic regions of the micelle, respectively.

In another embodiment, the biodegradable carrier platform is a particle. Various methods can be employed to formulate and infuse or load the particles with growth factors. Representative methods include, but are not limited to, water/oil/water or water/oil or water/water emulsion followed by solvent evaporation, electrohydrodynamic atomization (or electrospraying), piezo-assisted spraying, air-assisted jetting, super critical $CO_2$ and spray drying. In one example, the particles are prepared by a water/oil/water ($W_1/O/W_2$) double emulsion method. In the $W_1$ phase, a first aqueous phase is dispersed into the oil phase consisting of polymer (or other platform) dissolved in organic solvent (e.g., dichloromethane) and the growth factor(s) using a high-speed homogenizer. Examples of polymers include, but are not limited to, poly(L-lactide-co-glycolide) (PLGA), poly(D,L-lactide-co-glycolide), poly(L-lactide), poly(D,L-lactide) (PLA), poly($\epsilon$-caprolactone), poly(L-lactide-co-caprolactone), poly(D,L-lactide-co-caprolactone), cross-linked poly(ethylene glycol) (PEG), PLA-PEG co-polymers, poly-ester-amide co-polymers (PEA), and polyphosphazines. The primary water-in-oil (W/O) emulsion is then dispersed in a second aqueous solution containing a polymeric surfactant, e.g., poly(vinyl alcohol) (PVA) or PEG, and further homogenized to produce a W/O/W emulsion. After stirring for several hours, the particles are collected by centrifugation or filtration. A microparticle can be in a range from about 1 μm to about 200 μm, preferably 5 μm to 15 μm. A nanoparticle can be in a range from between about 10 nm to about 1000 nm, preferably about 250 nm to about 750 nm. Particles may also be fabricated from, for example, dextran, alginate, cellulose, hyaluronan, chitosan, collagen, albumin, gelatin, or like materials.

In a preferred embodiment, the biodegradable carrier platform is a core-shell particle. In the context of this application, "core-shell" means that the particle has a shell and includes from one to several core(s). Core-shell particles can be formed using various techniques such as, for example, coaxial electrospraying. In one exemplary method of fabricating core-shell particles, a first liquid solution ($L_1$) may be supplied to an outer tube by a pump and a second different liquid solution ($L_2$) may be supplied to an inner tube by a pump to form the core-shell particles. Solution $L_1$ may be the precursor solution that forms the (hydrophobic or hydrophilic) "shell" while solution $L_2$ may be the precursor solution that forms the (hydrophilic or hydrophobic) "core" of the particles that will be eventually collected on a collection target as the electrospray system is being operated. By creating core-shell particles in which the "shell" and the "core" independently harbor different growth factors, different release profiles may be obtained as the core and shell independently erode after delivery to a treatment site over a period of time (condition dependent).

In one embodiment, a core-shell particle includes a shell, a first core, and a second core. A solution for the shell includes a hydrophobic polymer in a molecular weight range of between 200 Daltons and 500,000 Daltons and a concentration of between 0.01 mg/mL and 1000 mg/mL (weight percent), e.g., poly(lactide-co-glycolide) or poly($\epsilon$-caprolactone). A first solution used to fabricate the first core includes a hydrophilic polymer in a molecular weight range of between 200 Daltons and 1,500,000 Daltons and a concentration of between 0.01 mg/mL and 1000 mg/mL (weight percent), e.g., poly(ethylene glycol) or polyvinyl alcohol. Incorporated within the first solution is a growth factor, such as vascular endothelial growth factor at a concentration of between 0.010 μg/mL to about 10,000 μg/mL. A second solution used to fabricate the second core also includes a hydrophilic polymer in a molecular weight range of between 200 Daltons and 1,500,000 Daltons and a concentration of between 0.01 mg/mL and 1000 mg/mL (weight percent), e.g., poly(ethylene glycol) or polyvinyl alcohol. Incorporated within the second solution is a growth factor, such as hepatocyte growth factor at a concentration of between 0.010 μg/mL to about 10,000 μg/mL. The particle may be fabricated such that the release of vascular endothelial growth factor and hepatocyte growth factor are simultaneously or sequentially released. Release will depend on the chemical and/or physical nature of the platform (e.g., polymer) used as well as parameters such as, but not limited to, molecular weight, concentration, and the addition or absence of excipients within the solution(s).

In some embodiments, the biodegradable carrier platform is a microfiber or nanofiber. For example, the treatment agent-infused microfiber can be formulated by electrospinning. "Electrospinning" is a process by which microfibers are formed by using an electric field to draw a polymer solution from the tip of a capillary to a collector. A voltage is applied to the polymer solution which causes a stream of solution to be drawn toward a grounded collector. Electrospinning generates a web of fibers which can be subsequently processed into smaller lengths.

Examples of sustained-release polymers which can be used in electrospinning include, but are not limited to, PLGA copolymers, PLA, poly($\epsilon$-caprolactone) or PLA-PCL co-polymers, PEA, PEG copolymers, polyurethanes, polyurethane ureas, polyphosphazines and collagen. In one method, the treatment agent is mixed with a bioerodable polymer solution, a solvent and a surfactant. Examples of surfactants can include, but are not limited to, anionic or cationic surfactants. Useful anionic surfactants include, but are not intended to be limited to, bis(2-ethylhexyl)sodium sulfosuccinate (AOT), bis(2-ethylhexyl)phosphate (Na-DEHP), tauroglycocholate, and sodium lauryl sulfate. A useful cationic surfactant is tetradecyltrimethyl-ammonium bromide (TTAB). Other surfactants include polyvinyl alcohol, polysorbates (e.g., TWEEN® types) and poloxamers (e.g., PLURONIC® types). Examples of a solvent include, but are not limited to, hexafluoroisopropanol, acetone, or tetrahydrofuran/dimethyl acetamide blends. The treatment agent-infused polymer solution is then subjected to electrospinning. As the solvent evaporates during electrospinning, the treatment agent incorporates and distributes within the polymer by non-covalent interactions. The resultant microfibers which can be from about 0.05 μm to about 20 μm in diameter form a web which may then be subsequent processed into smaller lengths of about 5 μm to about 500 μm.

In one embodiment, fibers can be processed or electrospun from a collagen and elastin solution in hexafluoroisopropanol (HFP). A treatment agent (e.g., growth factor) can be added to the biopolymer solution. A surfactant and a stabilizer can be used to evenly disperse the treatment agent in the solvent. The polymer solution can then be loaded into a syringe and placed in a syringe pump for metered dispensing at a predetermined rate. A positive output lead of a high voltage supply can be attached to a needle on the syringe. The needle can be directed to a stainless steel grounded target placed approximately 5-20 cm from the needle tip, which can be rotated at a predetermined speed to ensure an even coating. The distance of the needle from the target can be varied depending upon the diameter of the fibers needed. The resultant microfibers are from about 0.05 μm to about 20 μm in diameter and the resulting non-woven mat of fibers can then be processed into smaller lengths of about 5 μm to about 500 μm.

In another embodiment, the bioerodable carrier platform is a hydrogel, i.e., a bioscaffolding. A bioscaffolding may be a single component or multi-component hydrogel fabricated from a single precursor or multiple precursors. In one embodiment, a bioscaffolding formed of multiple precursors may include two precursors which are in a liquid state before mixing, and then a semi-solid gel-like state upon co-mixing thereof by a mechanism such as, for example, physical or chemical cross-linking. Examples of hydrogels include, but are not limited to, hyaluronic acid or a salt thereof, fibrin glue, alginate, PEG copolymers, and silk-elastin copolymers. One of ordinary skill in the art will appreciate that the treatment agents may be dispersed throughout, and therefore associated with, any of the single or multi-component precursor solution(s).

In a still further embodiment, the bioerodable carrier platform is a lipid-coated microbubble (LCM) including the peptide. Peptides can be incorporated into the microbubbles in a number of different ways, including binding of a peptide to the microbubble shell and attachment of site-specific ligands. Perfluorocarbon-filled albumin microbubbles avidly bind proteins and synthetic peptides and are sufficiently stable for circulating in the vasculature as blood pool agents. These microbubbles act as carriers of these agents until a site of interest is reached. Ultrasound applied over the skin surface can then be used to burst the microbubbles at a treatment site, causing localized release of the peptide or protein. Albumin-encapsulated microbubbles have also demonstrated a property to adhere to a vessel wall. These microbubbles provide targeted delivery without the application of ultrasound. Microbubbles have also been shown to directly take up genetic material, such as plasmids and adenovirus, and phospholipid-coated microbubbles have a high affinity for certain drugs.

The mechanisms by which ultrasound facilitates the delivery of drugs and genes result from an interplay among the therapeutic agent, the microbubble characteristics, the target tissue, and the nature of ultrasound energy. The presence of microbubbles in the insonified field reduces the peak negative pressure needed to enhance delivery with ultrasound. This occurs because the microbubbles act as nuclei for cavitation, decreasing the threshold of ultrasound energy necessary to cause this phenomenon. The results of optical and acoustical studies have suggested the following mechanisms for microbubble destruction by ultrasound: gradual diffusion of gas at low acoustic power; formation of a shell defect with diffusion of gas; immediate expulsion of the microbubble shell at high acoustic power; and dispersion of the microbubble into several smaller bubbles.

In general, polymers and biomacromolecules suitable to fabricate the bioerodable carrier platform(s) include, but are not limited to, fibrin glue precursors, alginate gel precursors, combinations of fibrin glue and alginate glue precursors, small intestinal submucosa/urinary bladder de-cellularized matrix, synthetic poly(ethylene glycol)-based materials, poly (N-isopropylacrylamide) copolymers, elastomers such as polyurethanes, polyurethane-ureas, and cross-linkable poly (ester) copolymers, in addition to dextran, silk-elastin, and hyaluronate.

In some embodiments, polymers used in the fabrication of the bioerodable carrier platform may be surface-modified to attach ligands such as arginine-aspartate-glycine (RGD) to increase cell adhesion, spreading and influence differentiation of a particular cell into the appropriate cell phenotype. For example, polymer particles or fibers may be treated by radio frequency glow discharge under ammonia atmosphere to introduce amine groups onto the particle/fiber surface, which may be used to attach linear spacers (e.g., 1,4-diisocyanatobutane), which may in turn be used to attach RGD groups.

Treatment Agents

According to some embodiments, a bioerodable carrier platform may include at least two different treatment agents, such as growth factors. Growth factors participate in biochemical signaling pathways to induce cell migration, differentiation, survival, or proliferation. Signaling occurs through binding of factors to cell surface specific receptors. Signals can be amplified within the cell to regulate specific gene expression. Growth factors typically act in a dose- and time-dependent fashion with small variations in concentrations resulting in a biological effect. When applied in post-MI therapies, growth factors have the potential to increase the survival of cells whether the cells are endogenous or exogenous. It is anticipated that the application of at least two growth factors to an injury site, e.g., compromised cardiac tissue caused by, for example, myocardial infarction or ischemic heart failure, may better mimic and induce the complex growth factor signaling pathways necessary to improve cardiac function. In vitro results have demonstrated that multiple growth factors cause a synergistic effect on cultured cells, i.e., the effect of two factors is greater than the sum of their two-fold effect.

Examples of growth factors include, but are not limited to, vascular endothelial cell growth factor (VEGF), basic fibroblast growth factor (bFGF), platelet-derived growth factor (PDGF), platelet-derived endothelial growth factor (PDEGF), insulin-like growth factor-1 (IGF-1), insulin-like growth factor-2 (IGF-2), transforming growth factor-alpha (TGF-α), transforming growth factor-beta (TGF-β), hepatocyte growth factor (HGF), stem cell factor, stromal derived growth factor-1-alpha (SDF-1α), hematopoietic growth factor or granulocyte colony-stimulating factors (G-CSF), granulocyte macrophage colony-stimulating factors (GM-CSF), nerve growth factor (NGF), growth differentiation factor-9 (GDF9), epidermal growth factor (EGF), neurotrophins, erythropoietin (EPO), thrombopoieten (TPO), myostatin (GDF-8), leukemia inhibitory factor (LIF), tumor necrosis factor-alpha (TNF-α), sonic hedgehog (Shh) protein (an upstream growth factor regulator).

In one embodiment, at least two growth factors can be associated with a bioerodable carrier platform to target a particular response (or "effect" or "function") useful for treating compromised cardiac tissue, such as a post-MI or HF region. Specific growth factors can produce a specific response from specific cells or tissue types. The response may include one of cell survival, angiogenesis, cell recruitment (or homing), anti-fibrotic development, and/or extracellular matrix production.

Endogenous cardiomyocyte (myocytes) apoptosis is the major etiological factor of wall thinning and chamber dilation and may ultimately lead to progression of cardiac myopathy. After an infarction, mature myocytes of an adult are not regenerated which can lead to significant thinning in the infarct region. Thus, factors which promote cell survival and cell recruitment applied to the infarct region are believed to be beneficial.

Angiogenesis, which is the promotion or causation of the formation of new blood vessels, is useful for treatment of a post-MI region for a number of reasons. After an MI, the infarct tissue as well as the border zone and the remote zone around the infarct tissue begin to remodel. Scar tissue forms in the infarct region as the granulation is replaced with collagen. Stress from blood pressure cause the scar to thin out and stretch. The perfusion in this region is typically 10% of the healthy zone, decreasing the number of active capillaries. Increasing the number of capillaries may lead to an increase in compliance of the ventricle due to filling up with blood.

Other benefits of increasing blood flow to the infarcted region include providing a route for circulating stem cells to seed and proliferate in the infarct region. Angiogenesis may also lead to increased oxygenation for the surviving cellular islets within the infarct region, or to prime the infarct region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well.

Fibrosis is the formation or development of excess fibrous connective tissue in an organ or tissue as a reparative or reactive process, as opposed to a formation of fibrous tissue as a normal constituent of an organ or tissue. Excess formation of fibrous connective tissue on the heart may force the heart to work harder following a post-MI incident, thus impairing the restorative process. Thus, factors which decrease production of excess fibrous connective tissue post-MI and applied to the infarct region are believed to be beneficial.

The myocardial extracellular matrix (ECM) consists of macromolecules, primarily produced locally from fibroblasts, and includes a fibrillar collagen network, a basement membrane and proteoglycans. The ECM of the heart was once believed to be an inert scaffold for cardiomyocytes but is now known to play an important role in LV remodeling. Excess production of fibrillar collagen in the ECM post-MI can cause myocardial stiffness which in turn causes the heart to have to work harder. As a result, factors which influence the ECM and its respective constituents applied to the infarct region are believed to be beneficial.

In one embodiment, simultaneous release of two growth factors may be used to boost a single desired growth factor action or to product multi-potent effects at an injury site such as a post-MI region. In one example, cell survival may be enhanced by the simultaneous release of (i) insulin-like growth factor-1 and hepatocyte growth factor, or (ii) insulin-like growth factor 1 and stem cell factor from a bioerodable carrier platform. In another example, angiogenesis may be enhanced by simultaneous release of (i) vascular endothelial growth factor and platelet-derived growth factor, (ii) vascular endothelial growth factor and hepatocyte growth factor, (iii) vascular endothelial growth factor and stem cell factor, (iv) basic-fibroblast growth factor and hepatocyte growth factor, (v) basic-fibroblast growth factor and stem cell factor, (vi) insulin-like growth factor 1 and basic-fibroblast growth factor; (vii) granulocyte colony-stimulating factor and hepatocyte growth factor from a bioerodable carrier platform. In another example, cell recruitment may be enhanced by simultaneous release of (i) granulocyte colony-stimulating factor and hepatocyte growth factor, (ii) granulocyte colony-stimulating factor and stromal derived factor-1-alpha, (iii) granulocyte colony-stimulating factor and stem cell factor, or (iv) granulocyte colony-stimulating factor and insulin-like growth factor 1 from a bioerodable carrier platform. Any of the above examples may be referred to as a binary simultaneous release formulation. In some embodiments, the binary simultaneous release formulation may include sonic hedgehog protein (shh).

For simultaneous release formulations, binary or multiple growth factors may be encapsulated in a suitable bioerodable carrier platform(s), such as liposomes, polymerosomes, micelles, particles (e.g., microparticles, nanoparticles, core-shell particles), nanofibers, or hydrogels. Simultaneous release formulations may be designed to produce similar release profiles over similar time spans of therapeutic doses of the growth factors. When delivered to an injury site (e.g., post-MI infarct site or ischemic/chronic HF site) of a patient, simultaneous delivery of the growth factors may be achieved by fabricating a formulation which encapsulates different growth factors within similar or the same platform. For example to achieve simultaneous release, at least two different growth factors may be encapsulated within the same particle or, alternatively, within two different particles of the same or substantially the same composition, size, and porosity. In some embodiments, simultaneous release of the at least two treatment agents may be in a time interval of between ten seconds and 8 weeks or more.

In another embodiment, sequential release of two growth factors may be used to boost a single desired growth factor action or to product multi-potent effects at an injury site (e.g., post-MI infarct site or ischemic/chronic HF site). Sequential release may be beneficial in the case when the second factor's effect is dependent on the action of the first growth factor, or, alternatively, warranted at a later point in time. In one example, cell survival followed by cell homing may be enhanced by the sequential release of (i) insulin-like growth factor 1 followed by stromal derived factor-1-alpha, (ii) insulin-like growth factor 1 followed by stem cell factor, (iii) insulin-like growth factor 1 followed by hepatocyte growth factor, or (iv) insulin-like growth factor 1 followed by granulocyte colony-stimulating factor from a bioerodable carrier platform. In another example, anti-fibrobotic development followed by angiogenesis may be enhanced by sequential release of (i) hepatocyte growth factor followed by vascular endothelial growth factor, or (ii) hepatocyte growth factor followed by basic-fibroblast growth factor from a bioerodable carrier platform. In another example, angiogenesis may be enhanced by sequential release of (i) vascular endothelial growth factor followed by platelet-derived growth factor, or (ii) vascular endothelial growth factor followed by angiopoietin-I from a bioerodable carrier platform. In another example, cell recruitment followed by cell survival may be enhanced by sequential release of (i) stromal derived factor-1-alpha followed by insulin-like growth factor-1, (ii) stem cell factor followed by insulin-like growth factor 1, or (iii) granulocyte colony-stimulating factor followed by insulin-like growth factor 1 from a bioerodable carrier platform. In another example, cell recruitment followed by angiogenesis may be enhanced by sequential release of (i) stromal derived factor-1-alpha followed by vascular endothelial growth factor (ii) stem cell factor followed by vascular endothelial growth factor, (iii) stem cell factor followed by basic-fibroblast growth factor; or (iv) granulocyte colony-stimulating factor followed by basic-fibroblast growth factor from a bioerodable carrier platform. Any of the above examples may be referred to as a binary sequential release formulation. In some embodiments, the binary sequential release formulation may include sonic hedgehog protein. It should be appreciated that embodiments of the invention encompass simultaneous or sequential release of more than two growth factors, or multiple simultaneous or sequential release formulation(s).

For sequential growth factor formulations, each growth factor may be encapsulated in a suitable combination of bioerodable carrier platforms, such as liposomes, polymerosomes, micelles, particles (e.g., microparticles, nanoparticles, core-shell particles), nanofibers, or hydrogels. Alternatively, each growth factor may be associated with a different component of a single bioerodable carrier platform. In the context of this application, "component" means a different physical or chemical portion of the same platform. Sequential release formulations may be designed to release one growth factor at a faster rate than release of a second growth factor. This may be achieved, for example, through use of different encapsulation (association) methods, such as liposomes for quick release and microparticles for longer, sustained release. Additionally, adjusting polymer compositions (e.g., PEG for one growth factor and PLGA for a different growth factor) and/or molecular weights of the carrier platform(s) (e.g., in the case of polymer-based carriers) present other means with which to vary release and/or degradation rates between different particles containing different growth factors. In some embodiments, a first bioerodable carrier platform is capable of release of a first growth factor in a time interval of between 10 seconds and 2 weeks and a second different bioerodable carrier platform is capable of release of the second different growth factor in a time interval of between 10 seconds and 10 weeks. For example, in an embodiment including microparticles and liposomes, the time interval for release of the liposome may be between about 10 seconds and 24 hours, while the time interval for the release of the microparticle may be between about 10 seconds and 10 weeks. In another embodiment, a single bioerodable platform, such as an electrosprayed core-shell particle, may be used for sequential release.

In some embodiments, a binary (or multiple) release formulation as described above may include additional treatment agent(s). In one example, the formulation may include an inhibitor of matrix metallopeptidase 9 (MMP-9). Matrix metalloproteinases are proteolytic enzymes which are believed to be involved in the process of cardiac remodeling following an MI. Early experimental studies have shown that a matrix metalloproteinase inhibitor is effective in reversing the left ventricle remodeling process which may ultimately lead to heart failure. Therefore, it is anticipated that addition of an inhibitor of MMP-9 to binary (or multiple) release formulations will have an increased beneficial effect on the injury site. Examples of MMP-9 inhibitors include, but are not limited to, tissue inhibitor of metalloproteinase-1 (TIMP-1), TIMP-3, TIMP-4, nobiletin, indole-3-carbinol, batimastate, marimastat, solimastat, neovastat, Bay 12-9566, AG3340, COL-3, BMS-275291, or CGS27023A.

In some embodiments, a binary (or multiple) release formulation as described above may include a specific IGF-1 isoform such as major extrahepatic insulin-like growth factor-1 (mIGF-1). mIGF-1 is naturally abundant in skeletal muscles and is believed to be more effective for cardiac muscle regeneration relative to other IGF-1 isoforms. At least one study has shown that mIGF-1 has the ability to modulate the inflammatory response with minimum scar formation. See Musaro, A., et al., *The Role of local Insulin-like Growth Factor-1 Isoforms in the Pathophysiology of Skeletal Muscle*, Current Genomics, vol. 3, pp. 149-162 (2002).

In some embodiments, a binary (or multiple) release formulation as described above may include a cardiovascular treatment agent useful in the treatment of compromised cardiac tissue. Examples of such cardiovascular treatment agent include, but are not limited to, antiplatelet drugs (e.g., aspirin, clopidogrel, ticlopidine, cilostazol, abciximab, eptifibatide, tirofiban, dipyridamole); beta blockers (e.g., aprenolol, carteolol, levobunolol, mepindolol, metapranolol, nadolol, oxprenolol, penbutolol, pindolol, propranolol, sotalol, timolol, acebutalol, atenolol, betaxolol, bisoprolol, esmolol, metprolol, nebivolol, carvedilol, celiprolol, labetalol, butaxamine); angiotensin-converting enzyme (ACE) inhibitors (e.g., captopril, enalapril, ramipril, quinapril, perindopril, lisinopril, benazepril, fosinopril, casokinins, lactokinins); statins (e.g., atorvastatin, cerivastatin, fluvastatin, lovastatin, mevastatin, pitavastatin, pravastatin, rosuvastatin, simvastatin, simvastatin/ezetimibe combination, lovastatin/niacin extended release combination, i.e., ADVICOR by Abbott Laboratories, Illinois, U.S., atorvastatin/amlopidine besylate, mesylate, or maleate combination), omega-3 fatty acids (natural or synthetic); or aldosterone antagonists (e.g., eplerenone).

Methods of Treatment

Techniques for delivering a binary (or multiple) release formulation according to embodiments of the invention to an injury site include, but are not limited to, percutaneous delivery, such as intra-coronary delivery, intra-myocardial delivery, and periadventitial delivery, in addition to delivery through an open chest procedure. Intra-coronary delivery includes antegrade arterial delivery, which typically involves routing a catheter through the arterial vasculature, and retrograde venous delivery, which typically involves routing a catheter through the venous vasculature. In intra-coronary delivery, the binary (or multiple) release formulation is delivered in the vasculature system adjacent the infarct region and its respective border zone. In intra-myocardial delivery, the binary (or multiple) release formulation is delivered directly into the ventricular wall by a needle. Periadventitial delivery refers to delivery of drugs from across the adventitia of arteries as well as delivery in the pericardial sac.

Figure 1B:
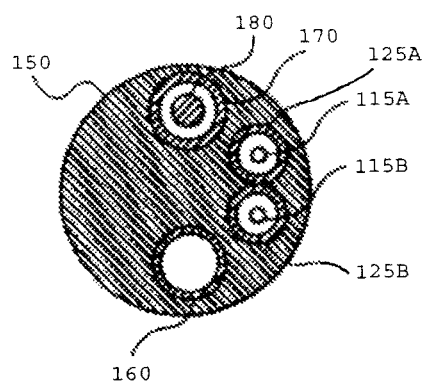
Figure 1C:
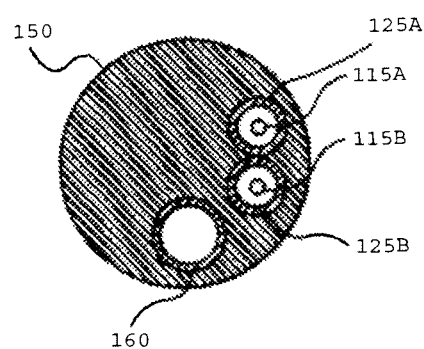

FIGS. 1A-1C illustrate an embodiment of a needle injection device which may be used to deliver a binary (or multiple) release formulation in accordance with embodiments of the invention. In general, the catheter assembly 100 provides a system for delivering substances to or through a desired area of a blood vessel or organ, such as a coronary artery or the heart, in order to treat a post-MI region or ischemic HF region. The catheter assembly 100 is similar to the catheter assembly described in commonly-owned, U.S. Pat. Nos. 7,179,249 and 6,554,801, titled "Directional Needle Injection Drug Delivery Device and Method of Use," by Steward, J. et al. which are incorporated herein by reference.

In one embodiment, catheter assembly 100 is defined by elongated catheter body 150 having proximal portion 120 and distal portion 110. Guidewire cannula 170 is formed within catheter body (from proximal portion 110 to distal portion 120) for allowing catheter assembly 100 to be fed and maneuvered over guidewire 180. Balloon 130 is incorporated at distal portion 110 of catheter assembly 100 and is in fluid communication with inflation cannula 160 of catheter assembly 100.

Balloon 130 may be formed from balloon wall or membrane 135 which is selectively inflatable to dilate from a collapsed configuration to a desired and controlled expanded configuration. Balloon 130 may be selectively dilated (inflated) by supplying a fluid into inflation cannula 160 at a predetermined rate of pressure through inflation port 165 (located at proximal end 120). Balloon wall 135 is selectively deflatable, after inflation, to return to the collapsed configuration or a deflated profile. Balloon 130 may be dilated (inflated) by the introduction of a liquid into inflation cannula 160. Liquids containing treatment and/or diagnostic agents may also be used to inflate balloon 130. In one embodiment, balloon 130 may be made of a material that is permeable to such treatment and/or diagnostic liquids. To inflate balloon 130, the fluid may be supplied into inflation cannula 160 at a predetermined pressure, for example, between about one and 20 atmospheres. The specific pressure depends on various factors, such as the thickness of balloon wall 135, the material from which balloon wall 135 is made, the type of substance employed and the flow-rate that is desired. In some embodiments, a balloon may be necessary to temporarily occlude a blood vessel so that the natural flow of blood does not interrupt the procedure by preventing proper placement of the injection needle. In other embodiments, a balloon may be necessary to localize the injection needle near the target region, or compromised heart tissue.

In this embodiment, catheter assembly 100 also includes at least two substance delivery assemblies 105a and 105b (not shown; see FIGS. 1B-1C) for injecting a binary (or multiple) release formulation to a myocardial infarct region or other treatment region. In one embodiment, substance delivery assembly 105a includes needle 115a movably disposed within hollow delivery lumen 125a. Delivery assembly 105b includes needle 115b movably disposed within hollow delivery lumen 125b (not shown; see FIGS. 1B-1C). Delivery lumen 125a and delivery lumen 125b each extend between distal portion 110 and proximal portion 120. Delivery lumen 125a and delivery lumen 125b may be made from any suitable material, such as polymers and copolymers of polyamides, polyolefins, polyurethanes and the like. Access to the proximal end of delivery lumen 125a or delivery lumen 125b for insertion of needle 115a or 115b, respectively is provided through hub 135 (located at proximal end 120). Delivery lumens 125a and 125b may be used to deliver a binary (or multiple) release formulation to a post-myocardial infarct region. In some embodiments, it may be helpful to maximize distribution of the formulation by using a dual needle catheter. It should be appreciated, however, that a single needle catheter and a non-needle catheter may be appropriate for delivery of a binary (or multiple) release formulation. Intracoronary delivery methods typically utilize non-needle-based catheters while intra-myocardial delivery methods typically utilize needle-based catheters.

FIG. 1B shows a cross-section of catheter assembly 100 through line A-A' of FIG. 1A (at distal portion 110). FIG. 1C shows a cross-section of catheter assembly 100 through line B-B' of FIG. 1A. In some embodiments, delivery assemblies 105a and 105b are adjacent to each other. In the case where the biodegradable carrier platform is a two-component hydrogel, the proximity of delivery assemblies 105a and 105b allows each component of the hydrogel to rapidly gel when delivered to a treatment site, such as a post-myocardial infarct region.

Figure 2:
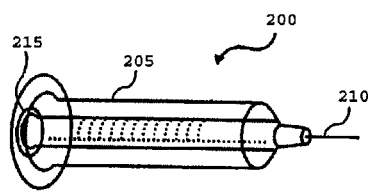
FIG. 2 illustrates an embodiment of a syringe which may be used pursuant to embodiments of the invention.

FIG. 2 illustrates an embodiment of a syringe which may be used pursuant to embodiments of the invention. Syringe 200 may include a body 205, a needle 210 and a plunger 215. A shaft of plunger 215 has an exterior diameter slightly less than an interior diameter of body 205 so that plunger 215 may, in one position, retain a substance in body 205 and, in another position, push a substance through needle 210. Syringes are known by those skilled in the art. In some applications, syringe 200 may be applied directly to a treatment site during an open-chest surgery procedure to deliver core-shell particles to a treatment site.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A method of treating compromised cardiac tissue within a mammal, comprising:
   advancing a delivery device through a lumen of a blood vessel to a treatment region wherein the treatment region is compromised cardiac tissue; and
   introducing through the delivery device:
      a first bioerodable carrier platform capable of sustained release of a first growth factor;
      at least one second different bioerodable carrier platform capable of sustained release of a second growth factor, wherein the second different bioerodable carrier platform is a two-component hydrogel selected from the group consisting of hyaluronic acid, fibrin glue, alginate and silk-elastin copolymers and wherein the second bioerodable carrier platform is formed upon separately delivering two precursors of the two-component hydrogel to the compromised cardiac tissue, wherein the two precursors are in a liquid state prior to delivering and mix to form the two-component gel after delivering; and
      at least one cell type,
   wherein a rate of release of the first growth factor from the first bioerodable carrier platform is faster than a rate of release of the second growth factor from the second bioerodable carrier platform, and
   wherein the first growth factor and the second growth factor are different and each of the first growth factor and the second growth factor have a different function when delivered to the compromised cardiac tissue such that cell survival followed by cell homing is enhanced.

2. The method of claim 1 wherein the at least one cell type is selected from the group consisting of localized cardiac progenitor cells, cardiac stem cells, mesenchymal stem cells, bone marrow derived mononuclear cells, adipose-derived stem cells, embryonic stem cells, umbilical cord blood derived stem cells, smooth muscle cells, skeletal myoblasts, endothelial progenitor cells and a combination thereof.

3. The method of claim 1 wherein the first carrier platform is one of a liposome, a polymersome, a micelle, a particle, a core-shell particle, a fiber, or a microbubble, wherein when the first carrier platform is a polymersome, or a particle, the carrier platform is fabricated from a material selected from the group consisting of, small intestinal submucosa/urinary bladder matrix, poly(ethylene glycol)-based materials, poly (N-isopropylacrylamide) copolymers, poly(D,L-lactide-co-glycolide), polyurethanes, polyurethane-ureas, poly(ester) copolymers, dextran, or a combination or a precursor thereof.

4. The method of claim 1 wherein the first growth factor and the second growth factor comprise one of: (i) insulin-like growth factor 1 and hepatocyte growth factor; (ii) insulin-like growth factor 1 and stromal derived factor-1-alpha; (iii) vascular endothelial growth factor and platelet-derived growth factor; (iv) vascular endothelial growth factor and hepatocyte growth factor; (v) vascular endothelial growth factor and stem cell factor; (vi) vascular endothelial growth factor and stromal derived factor-1-alpha (vii) basic-fibroblast growth factor and hepatocyte growth factor; (viii) basic-fibroblast growth factor and stem cell factor; (ix) insulin-like growth factor 1 and basic-fibroblast growth factor; (x) granulocyte colony-stimulating factor and hepatocyte growth factor; (xi) granulocyte colony-stimulating factor and hepatocyte growth factor; (xii) granulocyte colony-stimulating factor and stem cell factor; (xiii) granulocyte colony-stimulating factor and insulin-like growth factor 1, or (xiv) granulocyte colony-stimulating factor and stromal derived factor 1-alpha, the composition optionally including sonic hedgehog protein.

5. The method of claim 1 wherein the first growth factor and the second growth factor comprise one of: (i) insulin-like growth factor 1 and stromal derived factor-1-alpha; (ii) insulin-like growth factor 1 and hepatocyte growth factor; (iii) insulin-like growth factor-1 and stem cell factor, (iv) insulin-like growth factor 1 and granulocyte colony-stimulating factor; (v) hepatocyte growth factor and vascular endothelial growth factor; (vi) hepatocyte growth factor and beta-fibroblast growth factor; (vii) vascular endothelial growth factor and platelet-derived growth factor; (viii) vascular endothelial growth factor and angiopoietin-I; (ix) stem cell factor and insulin-like growth factor 1; (x) granulocyte colony-stimulating factor and insulin-like growth factor 1; (xi) stem cell factor and vasoendothelial growth factor; (xii) stem cell factor and beta-fibroblast growth factor; or (xiii) granulocyte colony-stimulating factor and beta-fibroblast growth factor, the composition optionally including sonic hedgehog protein.

6. The method of claim 4 or 5, further comprising, at least one of: (i) a matrix metallopeptidase 9 (MMP-9) inhibitor comprising one of tissue inhibitor of metalloproteinase-1 (TIMP-1), TIMP-3, TIMP-4, nobiletin, indole-3-carbinol, batimastat, marimastat, solimastat, neovastat, Bay 12-9566, AG3340, COL-3, BMS-275291, or CGS27023A; (ii) major extrahepatic insulin-like growth factor-1; or, (iii) a cardiovascular treatment agent selected from the group consisting of an antiplatelet drug, a beta blocker, an angiotensin-converting enzyme inhibitor, a statin, an omega-3 fatty acid, and an aldosterone antagonist.

7. The method of claim 1 wherein the first bioerodable carrier platform is capable of simultaneous release of the first growth factor and at least one treatment agent in a time interval of between 10 seconds and 10 weeks.

8. The method of claim 1 wherein the first bioerodable carrier platform is capable of release of the first growth factor in a time interval of between 10 seconds and 10 weeks and the second different bioerodable carrier platform is capable of release of the second growth factor in a time interval sequential to that of the first growth factor.

9. The method of claim 1 wherein the first bioerodable carrier platform is capable of release of the first growth factor in a time interval of between 10 seconds and 24 hours and the second different bioerodable carrier platform is capable of release of the second growth factor in a time interval sequential to that of the first growth factor.

10. The method of claim 1 wherein the first bioerodable carrier platform includes arginine-aspartate-glycine (RGD).

11. The method of claim 1 wherein the first bioerodable carrier platform is a liposome.

12. The method of claim 1 wherein the first growth factor comprises insulin-like growth factor 1.

13. The method of claim 11 wherein the second growth factor comprises stromal derived factor-1-alpha.

14. The method of claim 1 wherein the at least one cell type comprises cardiac progenitor cells.

\* \* \* \* \*

UNITED STATES PATENT AND TRADEMARK OFFICE
CERTIFICATE OF CORRECTION

| | | |
|---|---|---|
| PATENT NO. | : 8,703,180 B1 | Page 1 of 1 |
| APPLICATION NO. | : 11/877635 | |
| DATED | : April 22, 2014 | |
| INVENTOR(S) | : Stankus et al. | |

It is certified that error appears in the above-identified patent and that said Letters Patent is hereby corrected as shown below:

In the Claim,

Column 16, Claim 13, line 21, please delete "claim 11" and insert --claim 12--.

Signed and Sealed this
Fourteenth Day of October, 2014

Michelle K. Lee
*Deputy Director of the United States Patent and Trademark Office*